United States Patent [19]

Fisher et al.

[11] Patent Number: 5,019,578
[45] Date of Patent: May 28, 1991

[54] β-ADRENERGIC AGONISTS

[75] Inventors: Michael H. Fisher, Ringoes; Matthew J. Wyvratt, Jr., Mountainside, both of N.J.

[73] Assignee: Merck & Co., Inc., Rahway, N.J.

[21] Appl. No.: 506,312

[22] Filed: Apr. 9, 1990

Related U.S. Application Data

[63] Continuation of Ser. No. 185,637, Apr. 25, 1988, abandoned, which is a continuation-in-part of Ser. No. 126,987, Nov. 25, 1987, abandoned.

[51] Int. Cl.$^5$ .................. C07D 239/42; A61K 31/505
[52] U.S. Cl. ...................................... 514/275; 544/332
[58] Field of Search ......................... 544/332; 514/275

[56] References Cited

U.S. PATENT DOCUMENTS 4,358,455  11/1982  Atkinson et al. .................... 546/300

*Primary Examiner*—John M. Ford
*Attorney, Agent, or Firm*—David L. Rose; Joseph F. DiPrima

[57] ABSTRACT

The instant invention concerns certain α-heterocyclic ethanol amines wherein the amine group is substituted with various alkyl and unsaturated alkyl groups optionally further substituted with hydroxy, or alkoxy groups of the formula:

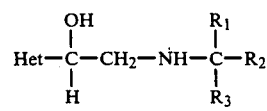

These compounds are useful as growth promotion agents in animals.

4 Claims, No Drawings

β-ADRENERGIC AGONISTS

This application is a continuation of Ser. No. 07/185,637, filed Apr. 25, 1988, now abandoned, which is a continuation-in-part of application Ser. No. 07/126,987, filed Nov. 25, 1987, now abandoned.

BACKGROUND OF THE INVENTION

In Atkinson U.S. Pat. No. 4,358,455 there are disclosed certain aralkyl amino ethanol heterocyclic compounds wherein the amino substituent is a phenyl alkyl group optionally substituted with various groups. The instant compounds are significantly different from the prior art compounds in eliminating the aryl or phenyl group.

SUMMARY OF THE INVENTION

The instant invention concerns certain α-heterocyclic ethanol amines wherein the amine group is substituted with various alkyl and unsaturated alkyl group optionally further substituted with hydroxy, or alkoxy groups. The compounds are potent β-agonist agents. Thus, it is an object of the present invention to describe such α-heterocyclic ethanol amine derivatives. A further object of this invention is to describe the various processes useful for the preparation of such compounds. A still further object is to describe the use of such compounds as growth promotion agents in animals. A further object is to describe compositions for such derivative as the active ingredient thereof. Further objects will become apparent from a reading of the following description.

DESCRIPTION OF THE INVENTION

The compounds of the instant invention are best represented by the following structural formula:

$$\text{Het}-\overset{\text{OH}}{\underset{\text{H}}{\overset{\blacktriangledown}{\text{C}}}}-\text{CH}_2-\text{NH}-\overset{R_1}{\underset{R_3}{\text{C}}}-R_2$$

wherein $R_1$, $R_2$ and $R_3$ are independently selected from hydrogen, loweralkyl, loweralkenyl, or loweralkynyl which may optionally be substituted with hydroxy, or loweralkoxy or $R_1$ and $R_2$ may be joined to form a cyclic ring of from 3 to 6 members which ring may further be substituted by lower alkyl;

Het is

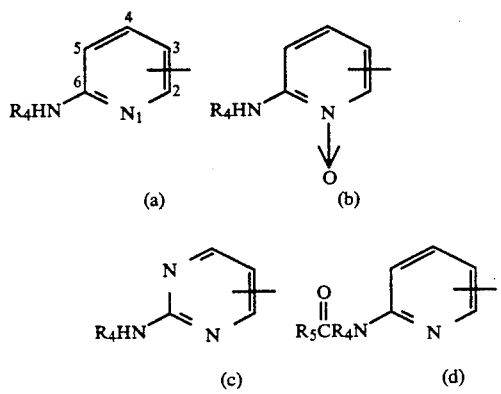

(a)     (b)

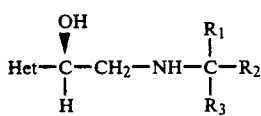

(c)     (d)

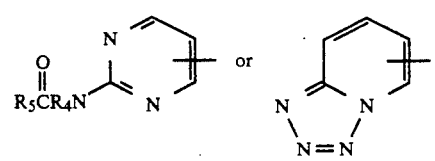

(e)     (f)

wherein $R_4$ and $R_5$ are independently hydrogen, loweralkyl, phenyl, substituted phenyl, phenylloweralkyl or substituted phenylloweralkyl where the substituent is loweralkyl, loweralkoxy or halo.

In the instant invention the term "loweralkyl" is intended to include those alkyl groups of either a straight or branched configuration of from 1 to 6 carbons exemplified by methyl, ethyl, propyl, isopropyl, butyl, sec-butyl, -pentyl, hexyl and the like.

The term "lower alkenyl" is intended to include those alkenyl groups of either a straight or branched configuration of from 2 to 6 carbon atoms exemplified by ethenyl, propenyl, butenyl, isobutenyl, pentenyl, hexenyl, and the like.

The term "lower alkynyl" is intended to include those alkynyl groups of either a straight or branched configuration of from 2 to 6 carbon atoms exemplified by ethynyl, propynyl, butynyl, pentynyl, hexynyl, and the like.

The term "loweralkoxy" is intended to include those alkoxy groups of either a straight or branched configuration of from 1 to 6 carbon atoms exemplified by methoxy, ethoxy, propoxy, isopropoxy, butoxy, pentoxy, isopentoxy, hexoxy, and the like.

The term "halogen" or "halo" is intended to include the halogen atoms of fluorine, chlorine, bromine and iodine.

The stereospecific configuration in the above structural formula indicates that the instant compounds possess the R-stereochemical configuration.

The preferred compounds of this invention are realized in the above structures wherein:

$R_1$, $R_2$ and $R_3$ are independently selected from hydrogen, loweralkyl, loweralkenyl or loweralkynyl or $R_1$ and $R_2$ may be joined to form a cyclic ring of from 3 to 6 members;

Het is selected from structures (a), (b), (c), (d), or (e);

$R_4$ is hydrogen or loweralkyl; and $R_5$ is loweralkyl of from 1 to 3 carbon atoms.

Further preferred compounds are realized in the above structures wherein:

$R_1$, $R_2$ and $R_3$ are independently selected from loweralkyl or $R_3$ is hydrogen or loweralkyl and $R_1$ and $R_2$ are joined to form a cyclic ring of 3 or 4 members;

Het is selected from structures (a), (b) or (c); and $R_4$ is hydrogen or loweralkyl of from 1 to 3 carbon atoms.

Still further preferred compounds are realized in the above structures wherein:

$R_1$, $R_2$ and $R_3$ are independently selected from loweralkyl of from 1 to 3 carbon atoms;

Het is structure (a) attached to the ethanol amine moiety at the 3 position as shown in the numbering of structure (a) above; and $R_4$ is hydrogen.

The compounds of this invention have one chiral center at the carbon atom of the ethanolamine bearing the hydroxy group and can have a second chiral center when the $R_1$, $R_2$ and $R_3$ groups are different. The chiral centers confer optical activity on the compounds.

Individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired R-isomer. Alternatively, the enantiomers may be separated on a chromatographic column containing an optically active support. In addition, the individual optical isomers may be prepared by asymmetric synthesis For example, the asymmetric center in the ethanolamine chain may be controlled by using a chiral reducing agent such as (R)-Alpine borane.

The R-stereochemistry at the 1-position of the ethanolamine group has been found to be particularly advantageous in the compounds of this invention. The R-stereochemistry is used to designate the hydroxy group as being above the plane of the instant compounds as follows:

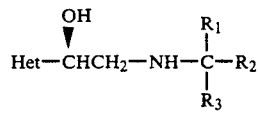

The R-isomer (with the hydroxy group above the molecular plane) is unexpectedly and significantly more active than the S isomer (with the hydroxy group below the plane) when the instant compounds are used as growth promotor agents. Thus the instant invention is directed to the R-stereoisomer significantly free of the S-isomer which offer the advantage of a compound possessing activity at a level many multiples that of the S-isomer and the added benefit that with a single, substantially pure isomer, drug residues, always a concern to regulatory agencies which consider the safety and efficiency of an animal health drug prior to its commercial release, will be significantly reduced from that of the racemic mixture.

The compounds of this invention when Het is structures (a), (b) when $R_4$ is hydrogen, or (f) are prepared according to the following reaction scheme:

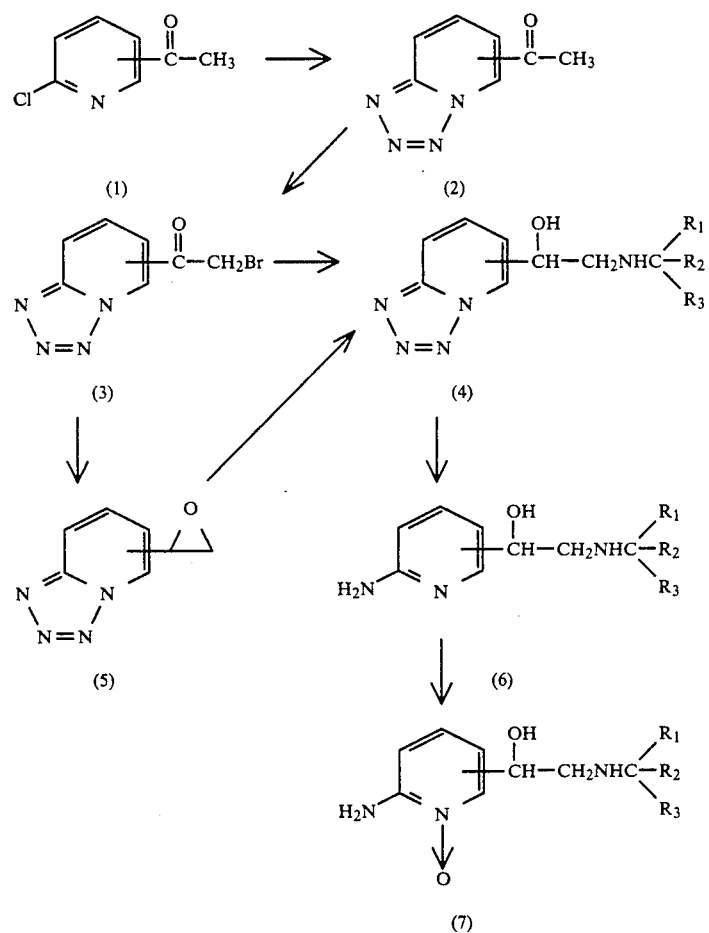

In the foregoing reaction scheme the starting material 2-chloro-acetyl pyridine (1) is treated with sodium azide to prepare the acetyl tetrazolo [1,5-a] pyridine (2). The reaction is carried out in a protic solvent such as an aqueous alcohol in the presence of an acid, preferably hydrochloric acid at from 50° C. to the reflux temperature of the reaction mixture. The reaction is generally complete in from about 5 to 24 hours. This step and the next step are also described in the Atkinson et al. patent.

In the next step the acetyl side chain of compound (2) is brominated with elemental bromine under acidic conditions such as hydrogen bromide or aluminum tribromide in acetic acid to prepare compound (3). The reaction may also be carried out using the analogous chloro reagents to prepare compound (3) with a chloro substituted acetyl group. The reaction is complete in from 1 to 5 hours and is generally carried out at from 0° C. to room temperature. Room temperature is preferred. Compound 3 may be sequentially aminated and reduced to form compound (4) or compound (3) may be reduced and treated with base to form an epoxide (5) which is then aminated to also prepare compound (4). The use of chiral reducing agents in this sequence allows the preparation of specific stereoisomers since the carbon atom bearing the hydroxy in compound (4) is asymmetric.

In the reaction of compound (3) to prepare compound (4) the starting material is placed in an aprotic solvent such as acetonitrile and excess amine ($H_2N-CR_1R_2R_3$) and stirred for from 10 minutes to 2 hours. The solvent is removed and the residue containing the aminated ketone intermediate, which is not isolated, is dissolved in a protic solvent such as an alcohol and combined with a mild reducing agent preferably sodium borohydride at from 0 to 10° C. for from 15 minutes to 2 hours. The product is isolated using known techniques.

Compound (3) may also be converted into the epoxide using a mild reducing agent such as sodium borohydride, lithium borohydride and the like. Such reducing agents will produce a racemic mixture of stereoisomers. Preferably a stereospecific reducing agent such as R-alpine borane may be used which will prepare the R-isomer of the epoxide substantially free of the S-isomer. The reaction is carried out in an inert solvent from 0° C. to room temperature, preferably at room temperature. The reaction is generally complete in from 1 to 10 days. The progress of the reaction is generally followed by taking aliquots of the reaction mixture and analyzing them for the presence of starting material using, for example, thin layer chromatography. Additional reducing agent may be added as needed. The reaction mixture is then treated with base, such as an alkali metal hydroxide, preferably sodium hydroxide in a protic solvent such as an alcohol or in the presence of a tertiary amine or with excess amine reactant ($H_2NCR_1R_2R_3$). The reaction is generally complete in from ½ to 24 hours at from 0° C. to room temperature, preferably room temperature.

The epoxide is aminated using excess amine in an alcohol heated at from 50° C. to reflux. The reaction is generally complete in from 1 to 24 hours. If compound (5) was prepared in a stereospecific manner the optical purity of the product, compound (4) will be preserved. If the amine component contains an asymmetric center (where none of $R_1$, $R_2$ or $R_3$ are identical) a mixture of diastereomers will then be produced. Separation of these diastereomers can be effected by chromatographic procedures or fractional crystallization. Alternatively, an optically pure amine may be used. Compound (4) has the Het group of structure (f).

The tetrazole ring of compound (4) may be removed to prepare the 2-amino pyridine, compound (6), in an alcohol solvent such as methanol with tin (II) chloride. The addition of one equivalent of hydrogen chloride will accelerate the reaction. The reaction is heated at from 50° C. to reflux, preferably reflux, for from 1 to 24 hours, affording structure (a) when $R_4$ is hydrogen.

Compound (6) may be oxidized to produce the pyridine-1-oxide wherein Het is structure (b) and $R_4$ is hydrogen. The reaction is carried out by protecting the amine and hydroxy groups with an acyl function, preferably a lower alkanoyl group such as acetyl. The acyl protecting groups are prepared using normal acylating techniques such as an acyl anhydride, preferably acetic anhydride. The oxidation is carried out using a mild oxidizing agent such as meta-chloroperbenzoic acid in a chlorinated hydrocarbon, preferably methylene chloride. The reaction is generally complete in from 1 to 4 hours at from 0° C. to room temperature, preferably room temperature. Slightly longer reaction times may be needed however, if larger or bulkier protecting groups are used. The protecting acyl groups are removed using acid or base catalyzed hydrolysis, preferably base catalyzed hydrolysis, following procedures well known to those skilled in the art.

The compounds of this invention wherein Het is structures (a), (b), (c), (d) or (e) are prepared according to the following reaction scheme wherein A in the heterocyclic ring represents a ring carbon atom or a nitrogen ring heteroatom.

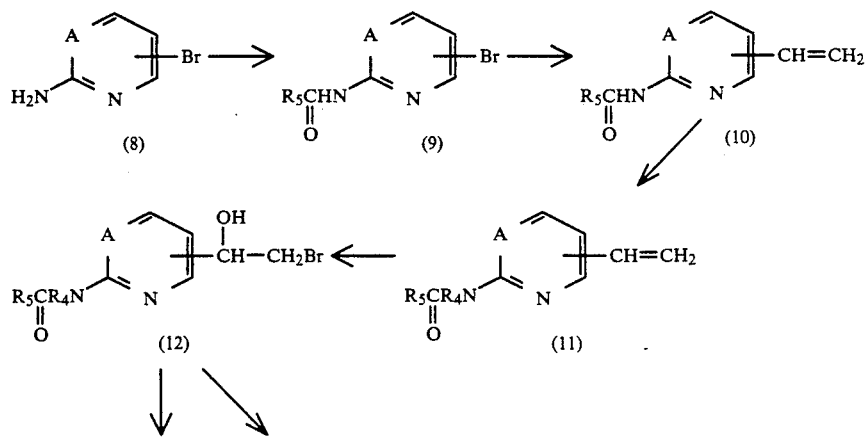

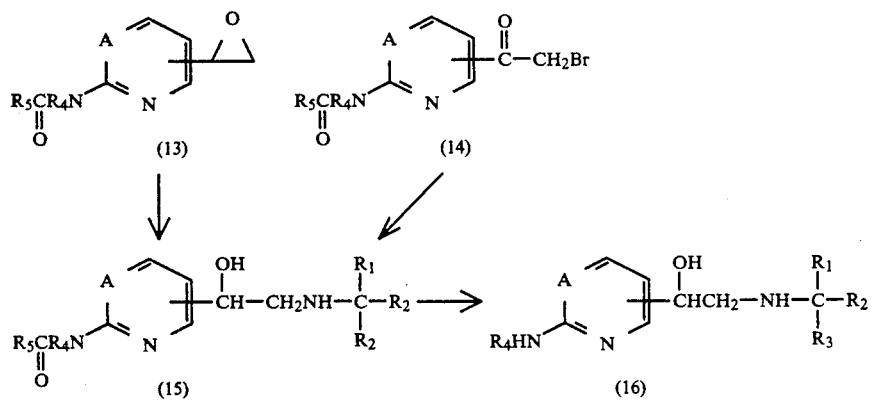

The starting material for this series of reactions starts with a 2-amino bromo pyridine or pyrimidine, compound (8). This compound is acylated at the 2-amine group to prepare compound (9). The reaction is carried out using acylating reagents such as anhydrides or acid chlorides in pyridine with 4-dimethylamino-pyridine as a catalyst. The reaction is generally complete in from 1 to 48 hours at from 0° C. to 100° C., preferably at 100° C.

Compound 9 is reacted in a pressure vessel to exchange the bromine with ethylene. The reaction is carried out in an inert solvent such as acetonitrile with triethylamine, tris(-O-tolyl) phosphine with catalytic palladium such as palladium acetate in an atmosphere of ethylene at a pressure of about 200 psiq (14,000 g/cm$^2$). The reaction is carried out at about 80° C. and is generally complete in about 12 to 24 hours.

At this point in the reaction scheme, if an R$_4$ substituent other than hydrogen is desired, such procedure is carried out on compound (10). The reaction is carried out in an aprotic solvent such as dimethylformamide in the presence of an alkali metal hydride, preferably sodium hydride and an R$_4$-halide. The reaction is carried out at from 0° C. to room temperature, preferably room temperature, and is generally complete in from 5 to 24 hours.

In the next step, compound (11) is converted to compound 12 by adding bromine and water across the exocyclic double bond. (If R$_4$ is hydrogen, this reaction is carried out directly on compound (10).) This reaction is carried out in an inert solvent such as tetrahydrofuran in the presence of water and N-bromosuccinimide. The reaction is carried out at about 0° C. to room temperature, preferably room temperature, and is generally complete in from 12 to 24 hours.

Compound (12) is then converted into the epoxide (13) by treatment with base, -preferably an alkali metal hydroxide such as sodium hydroxide in an alcohol solvent or in the presence of a tertiary amine. The reaction is generally complete in from 50 minutes to 24 hours at from 0° C. to room temperature, preferably room temperature.

Compound (12) may also be oxidized to the bromoketone compound (14) using an oxidizing agent such as manganese dioxide or Jones reagent, preferably manganese dioxide. The reaction is carried out in an aprotic solvent preferably a chlorinated hydrocarbon such as methylene chloride and is generally complete in from 30 minutes to 24 hours.

Compounds (13) and (14) are converted to the aminated products where Het is structure (d) or (e) by following the procedures used to prepare compound (4) from compounds (3) or (5) described above.

Compound (15) is hydrolyzed to compound (16), which is the product when Het structure (a) or (c), using acid or base catalyzed hydrolysis. Base catalyzed hydrolysis is preferred.

The desired R isomer may be isolated by either fractional crystallization with an optically pure acid or by chromatographic separation on a chiral column.

The compounds of this invention are capable of forming salts with various inorganic and organic acids and such salts are also within the scope of this invention. Typical acids are hydrochloric, hydrobromic, sulfuric, phosphoric, methanesulfonic, toluenesulfonic, maleic, fumaric, camphorsulfonic and the like. The non-toxic physiologically acceptable salts are preferred, although other salts are also useful, such as in isolating or purifyinq the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The compounds of this invention are useful as animal growth promotants. They can be used to increase the growth and feed efficiency of ruminant and non ruminant animals such as sheep, cattle, goats, horses, swine, chickens and the like. The active compound can be fed to the animal by incorporating it into the animal's feed or drinking water or it can be administered in a unit dosage form either orally as a drench, tablet, bolus or sustained release bolus or parenterally by injection or from a subcutaneous implant. The administration of the active compounds will produce a surprising increase in body weight, decrease in body fat and increase in body protein for the same food intake.

The active compounds can be administered to the animals at daily rates of from 0.001 to 10 mg/kg of body weight which may vary depending upon the particular animal being treated as well as the age and general physical condition of the animal. Preferably, daily dosages of from 0.01 to 1.0 mg/kg are utilized. When administered as part of the animal's feed or drinking water the active compound is present at rates of from 0.01 to 100 ppm which is determined to provide the appropriate daily amounts of the growth promotant compound.

At the same dosages listed above for growth promotion effects, substantial increases in feed efficiency are also observed.

EXAMPLE 1

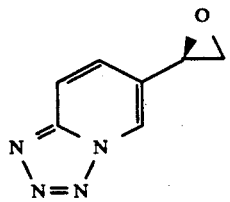

(R)-2-(tetrazolo[1,5-a]pyrid-6-yl)oxirane

In a 12-liter 3-necked flask under nitrogen, 304 g (1.26 mol) of 6-bromoacetyltetrazolo[1,5-a]pyridine was cooled with an ice-bath. By means of a large bore canulla, 4.8 liters (2.4 mol) of commercial 0.5 M (R)-Alpine Borane in tetrahydrofuran (Aldrich) was slowly added to the 6-bromoacetyltetrazolo[1,5a]pyridine mixture. A nitrogen inlet tube was submerged into the reaction solution and the reaction mixture permitted to warm to 30° C. (warm water bath). Nitrogen was passed through the solution until the reaction solution was approximately one third its original volume. The dark red solution was permitted to stir at room temperature for 3 days. Tlc (silica gel) of the reaction mixture indicated that starting material remained. An additional 200 ml of 0.5 M (R)-Alpine Borane was added and concentrated as above to its original volume. The reaction mixture was stirred an additional two days at room temperature. The reaction mixture was then added to 10 liters of a cold aqueous solution of sodium hydroxide (2.5 N) with vigorous stirring. To this mixture, 8 liters of methylene chloride was added and the layers separated. The aqueous layer was further extracted with methylene chloride and the combined organic layers backwashed with 2.5 N NaOH, water and brine. The methylene chloride solution was dried with anhydrous sodium sulfate and filtered through a silica gel plug. The filtrate was concentrated under reduced pressure. The residue was then chromatographed on a silica gel (5 Kg) column. The column was eluted first with methylene chloride and then with ethyl acetate:hexane (2:3 to 3:2). Concentration of the appropriate fractions gave 121 g of pure (R)-epoxide; IR (Nujol) =1640, 1510, 1245, 1200, 1150, 1095, and 830 cm$^{-1}$; ]$\alpha$]$^{25}$D = +6.5 (c=1, acetone). Optical purity was checked by reaction with (R)-$\alpha$-methyl benzylamine. Examination of the crude product by $^1$H NMR revealed only 3% of the (S)-isomer.

EXAMPLE 2

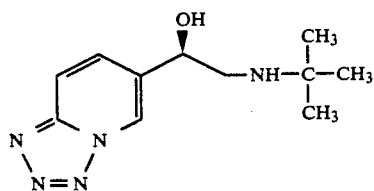

(R)-$\alpha$-[[(1,1-Dimethylethyl)amino]methyl]tetrazolo[1,5-a]pyridine-6-methanol A solution of 517 mg (3.19 mmol) of (R)-2-(tetrazolo[1,5-a]pyrid-6-yl)oxirane and 1.5 ml (14.9 mmol) of tert.-butyl amine in 10 ml of absolute ethanol was heated at reflux for 2 hours under nitrogen. The reaction mixture was concentrated under reduced pressure. The residue was dissolved in a minimum amount of methylene chloride and then diluted with hexane until cloudy. A precipitate formed which was collected by filtration to give 646 mg of crystalline product. This material was chromatographed on silica gel with a 90:10:1 methylene chloride:methanol:concentrated aqueous ammonium hydroxide solution. The appropriate fractions were combined and crystallized from ether/hexane to give 538 mg. (72%) of pure product. Treatment of an ethanolic solution of the free base with gaseous HCl gave the hydrochloride salt; [$\alpha$]$^{25}$D = −39.3° (MeOH, c=0,748); Analysis: Calc'd. for $C_{11}H_{17}N_5O \bullet HCl$:

C, 48.62; H, 6.68; N, 25.77; Cl, 13.05. Found: C, 48.55; H, 6.43; N, 25.82; Cl, 12.78.

EXAMPLE 3

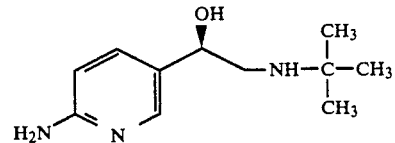

(R)-6-Amino-$\alpha$-[[(1,1-dimethylethyl)amino]methyl]-3-pyridinemethanol Z-2-butenedioate (1:2)

A solution of 538 mg (2.29 mmol) of (R)-$\alpha$-[[(1,1-dimethylethyl)amino]methyl]tetrazolo[1,5-a]- pyridine-6-methanol in 15 ml of methanol was treated with 0.19 ml (2.29 mmol) of concentrated hydrochloric acid and 1.03 g (4.58 mmol) of $SnCl_2 \bullet 2H_2O$. The reaction mixture was heated at reflux for one hour at which point tlc (silica gel) indicated completion. The mixture was reduced in volume under reduced pressure and then diluted with methylene chloride. The organic solution was washed with 15 ml of 2.5 N NaOH solution. The aqueous layer was back washed with a 20% methanolic methylene chloride solution until all product had been recovered. The combined organic layers were washed with saturated sodium chloride solution (2X), dried with anhydrous magnesium sulfate, and concentrated to dryness. The crude product was chromatographed on silica gel with 80:20:2 methylene chloride:methanol:concentrated aqueous ammonia as eluent to five 434 mg of pure product. To a solution of this free base (2.07 mmol) in 3 ml of absolute ethanol, a solution of 506 mg (4.36 mmol) of maleic acid in 5 ml of absolute ethanol was added slowly. The heterogeneous mixture was permitted to stir for an additional hour. The precipitate was collected by filtration and washed with ethanol-ether and then ether to give 690 mg of salt. The filtrate was diluted with ether to afford additional solid which was collected and rinsed with ethanol-ether and ether to afford 110 mg of product (total yield, 88%). A sample was recrystallized from ethanol, m.p. 167°-68° C. (dec.); [$\alpha$]$^{25}$D = −35.0 (MeOH); Analysis: Calc'd. for $C_{11}H_{19}N_3O \bullet 2C_4H_4O_4$:

EXAMPLE 4

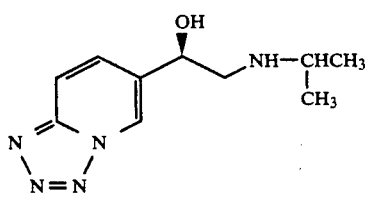

(R)-α-[[(1-Methylethyl)amino]methyl]tetrazolo[1,5-a]pyridine-6-methanol

In a sealed reaction tube, 250 mg (1.54 mmol) of (R)-2-(tetrazolo[1,5-a]pyrid-6-yl)oxirane and 450 mg (7.6 mmol) of isopropyl amine in 0.6 ml of absolute ethanol was heated at 100° C. (bath temperature) for two hours with stirring. The reaction mixture was concentrated under reduced pressure and the residue purified by preparative Tlc (silica gel; 90:10:2 ethyl acetate:methanol: triethylamine) to give 271 mg (79%) of pure tetrazole.

EXAMPLE 5

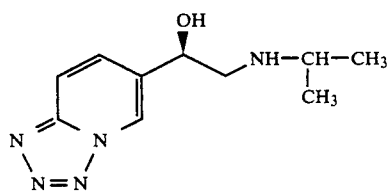

(R)-6-Amino-α-[[(1-methylethyl)amino]methyl]-3pyridine methanol dihydrochloride

A solution of 260 mg (1.18 mmol) of (R)-α-[[(1-methylethyl)amino]methyl]tetrazolo[1,5-a]pyridine-6-methanol in 25 ml of methanol was treated with 0.53 g (2.35 mmol) of SnCl$_2$•2H$_2$O. The mixture was heated at reflux for 28 hours and then concentrated to dryness under reduced pressure. The residue was dissolved in methylene chloride and treated with an aqueous 10% NaOH solution. The two-phase system was shaken for 15 minutes and the layers separated. The aqueous layer was repeatedly extracted with methylene chloride. The combined organic layers were dried with anhydrous sodium sulfate and concentrated. The residue was purified by preparative Tlc (silica gel; 80:20:3 ethyl acetate:methanol:triethylamine) to give 180 mg (67%) of product. This material was dissolved in absolute ethanol and treated with gaseous HCl to form the hydrochloride salt. Concentration under reduced pressure afforded an extremely hydroscopic solid (232 mg); $[\alpha]^{25}D = -45.3$ (MeOH); Analysis: Calc'd. for C$_{10}$H$_{17}$N$_3$O•2HCl:

C, 44.79; H, 7.14; N, 15.67; Cl, 26.44. Found: C, 45.04; H, 7.48; N, 15.45; Cl, 26.01.

EXAMPLE 6

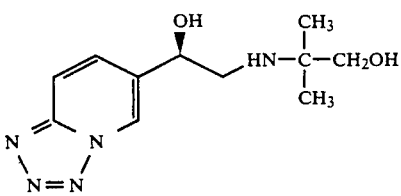

(R)-α-[[(1,1-Dimethyl-2-hydroxyethyl)amino]methyl]-tetrazolo[1,5-a]pyridine6 methanol A solution of (R)-2-(tetrazolo[1,5-a]pyrid 6-yl)oxirane (0.25 g, 1.54 mmol) and 2-amino-2-methyl-1-propanol (0.275 g, 3.08 mmol) in 1 ml of absolute ethanol in a sealed reaction tube was heated at 120° C. (bath temperature) for two hours. The reaction mixture was concentrated under reduced pressure and then purified by preparative Tlc (silica gel; 80:20:0.5 methylene chloride:methanol: concentrated NH$_4$OH) to afford 355 mg (92%) of product.

EXAMPLE 7

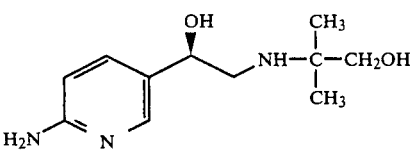

(R)-6-Amino-α-[[(1,1-dimethyl-2-hydroxyethyl)amino]methyl]-3-pyridinemethanol dihydrochloride A mixture of 355 mg of (R)-α-[[(1,1-dimethyl-2-hydroxyethyl)amino]methyl]tetrazolo[1,5-a]pyridine-6-methanol and 636 mg of SnCl$_2$•2H$_2$O in 25 ml of methanol was heated at reflux for 48 hours. The reaction mixture was concentrated under reduced pressure and the residue treated with 60 ml of 10% NaOH solution. This solution was then continually extracted with methylene chloride for 18 hours to give 240 mg of crude product. Purification by preparative Tlc (silica gel; 80:20:1.5 methylene chloride:methanol:concentrated NH$_4$OH) afforded 168 mg (53%) of product which was converted into its dihydrochloride salt in absolute ethanol. Concentration gave 211 mg of a hydroscopic solid; $[\alpha]^{25}D = -35.2$ (Me2OH, c=0.84).

EXAMPLE 8

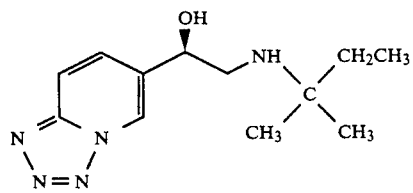

(R)-α-[[(1,1-Dimethylpropyl)amino]methyl]tetrazolo[1,5-a]pyridine-6-methanol

A solution of 250 mg (1.54 mmol) of (R)-2-(tetrazolo[1,5-a]pyrid-6-yl)oxirane and 663 mg (7.61 mmol) of tert amylamine in 0.6 ml of absolute ethanol in a pressure tube was heated at 100° C. (bath temperature)

for two hours. The reaction mixture was concentrated under reduced pressure to yield 369 mg of crude product which was used in the next reaction without further purification.

EXAMPLE 9

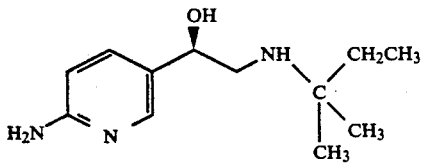

(R)-6-Amino-α-[[(1,1-dimethylpropyl)amino]methyl]-3-pyridinemethanol dihydrochloride To a solution of crude (R)-α-[[(1,1-dimethyl-propyl)amino]methyl]tetrazolo[1,5-a]pyridine-6-methanol (364 mg) in 32 ml of methanol, 683 mq of SnCl$_2$•2H$_2$O was added and the resulting mixture heated at reflux for 24 hours. The reaction mixture was concentrated under reduced pressure and the residue partitioned between methylene chloride and 10% aqueous NaOH solution. The alkaline phase was repeatedly extracted with methylene chloride. The combined organic layers were washed with saturated NaCl solution and dried with anhydrous magnesium sulfate. The solution was concentrated and the residue (347 mg) was chromatographed on silica gel plates (87:10:3 ethyl acetate:methanol:triethylamine) to give 281 mg of product. This material was dissolved in absolute ethanol, treated with excess ethanolic HCl and then diluted with ether. The hydrochloride salt was collected by filtration (168 mg); $[\alpha]^{25}D = -43.5$ (MeOH); Analysis: Calc'd. for C$_{12}$H$_{19}$N$_3$O•2HCl•½H$_2$O:

C, 47.53; H, 7.31; N, 13.86; C, 23.38. Found: C, 47.70; H, 7.54; N, 13.54; Cl, 23.44.

EXAMPLE 10

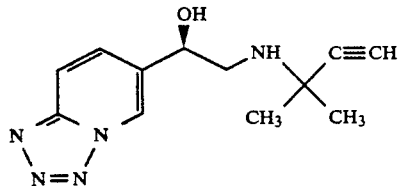

(R)-α-[[(1,1-Dimethyl-2-propynyl))amino]methyl]-tetrazolo[1,5-a]pyridine-6-methanol A solution of 250 mg of (R)-2-(tetrazolo-[1,5-a]pyrid-6-yl)oxirane and 703 mg of 1,1-dimethylpropargylamine in 0.6 ml of ethanol was heated at 100° C. (bath temperature) for two hours in a sealed tube. The reaction mixture was concentrated to afford a gummy solid, 351 mg. Tlc and $^1$H NMR were consistent with good purity and structural assignment.

EXAMPLE 11

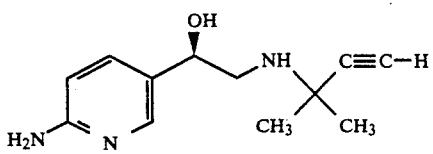

(R)-6-Amino-α-[[(1,1-dimethyl-2-propynyl)amino]-methyl]-3-pyridinemethanol dihydrochloride To a solution of crude (R)-α-[[(1,1-dimethyl-2-propynyl)amino]methyl]tetrazolo[1,5-a]pyridine-6-methanol (351 mg, 1.43 mmol) in 30 ml of methanol, 642 mg (2.85 mmol) of SnCl$_2$•2H$_2$O was added and the reaction mixture heated at reflux under nitrogen for 24 hours. The reaction mixture was concentrated and the residue partitioned between methylene chloride and 10% aqueous NaOH solution. The layers were separated and the aqueous layer repeatedly extracted with methylene chloride. The combined organic layers were backwashed with saturated NaCl solution, dried with anhydrous magnesium sulfate and concentrated to yield 296 mg of crude material. The product was purified by preparative Tlc on silica gel (77:20:3 ethyl acetate:methanol:triethylamine) to give 209 mg of pure product. This material was dissolved in absolute ethanol and treated with an ethanolic solution of HCl. The resulting solution was then added to ether and the precipitate which formed was collected by filtration and dried in a vacuum dessicator over phosphorous pentaoxide to yield 237 mg of the hydrochloride salt; $[\alpha]^{25}D = -34.5$ (MeOH); Analysis: Calc'd, for C$_{12}$H$_{17}$N$_3$O•2HCl:

C, 49.32; H, 6.55; N, 14.38; Cl, 24.27. Found: C, 49.54; H, 6.20; N, 14.06; Cl, 23.74.

EXAMPLE 12

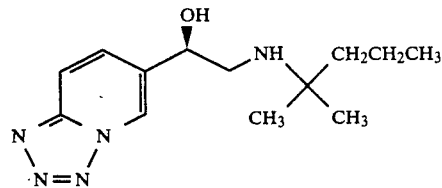

(R)-α-[[(1,1-Dimethylbutyl)amino]methyl]tetrazolo-[1,5-a]pyridine-6-methanol

A solution of 490 mq of (R)-2-(tetrazolo-[1,5-a]pyrid-6-yl)oxirane and 600 mg of tert-hexylamine in 10 ml of absolute ethanol was heated at reflux for 5.5 hours. The reaction mixture was concentrated under reduced pressure and the residue redissolved in methylene chloride. Hexane was added to this solution in order to precipitate out the tetrazole which was collected by filtration to give 530 mg of crude product. Purification on silica gel (90:10:1 methylene chloride:methanol: concentrated ammonium hydroxide) afforded 463 mg of tetrazole. This material was dissolved in methylene chloride, treated with charcoal and filtered through anhydrous magnesium sulfate. The filtrate was diluted with hexane and the precipitate collected by filtration, 396 mg; m.p. 122°-24° C.; Analysis: Calc'd. for C$_{13}$H$_{21}$N$_5$O:

C, 59.29; H, 8.04; N, 26.60. Found: C, 59.35; H, 8.01; N, 26.70.

EXAMPLE 13

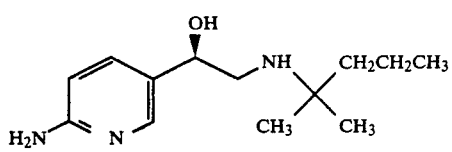

(R)-6-Amino-α-{[(1,1-dimethylbutyl)amino]methyl}-3-pyridinemethanol dihydrochloride To a suspension of 380 mg (1.45 mmol) of (R)-α[[(1,1-dimethylbutyl)amino]methyl]tetrazolo[1,5-a]-pyridine-6-methanol in 10 ml of methanol, 0.12 ml of concentrated HCl solution (1.44 mmol) and 695 mg (3.09 mmol) of SnCl$_2$•2H$_2$O were added and the resulting solution heated at reflux for 17 hours. The reaction mixture was concentrated under reduced pressure and the residue partitioned between 45 ml of methylene chloride and 3 ml of 2.5 N NaOH solution. The layers were separated and the aqueous layer extracted further with 20% methanol/methylene chloride. The combined organic layers were backwashed with saturated NaCl solution, treated with charcoal and then filtered through an anhydrous magnesium sulfate pad. The filtrate was concentrated to give 330 mg of product. This material was dissolved in ethanol and treated with an ethanolic solution of HCl. The solution was concentrated to dryness and the residue redissolved in methanol and diluted with ether to give the crystalline hydrochloride salt, 328 mg, m.p. 187°-88° C. (dec); $[\alpha]^{25}D = -40.0$; Analysis: Calc'd. for C$_{13}$H$_{23}$N$_3$O•2HCl:

C, 50.32; H, 8.12; N, 13.54. Found: C, 50.29; H, 8.43; N, 13.45.

EXAMPLE 14

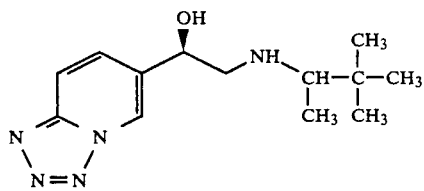

(R)-α-[[((R,S)-1-Methyl-2,2 dimethylpropyl)amino]methyl]tetrazolo[1,5-a]pyridine-6-methanol A solution of 375 mg of (R)-2-(tetrazolo[1,5-a]pyrid-6-yl)oxirane and 1.53 ml of 2 amino 3,3-dimethylbutane in 0.9 ml of absolute ethanol was heated at reflux for 5 hours under nitrogen. The reaction mixture was concentrated under reduced pressure and the residue purified by preparative Tlc on silica gel (95:5:1 methylene chloride:methanol: NH$_4$OH) to afford two isomers: Isomer A, 263 mg; Isomer B, 243 mg.

EXAMPLE 15

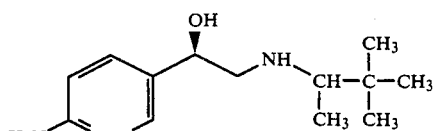

(R)-6-amino-α- [[((R,S)-1-methyl-2,2-dimethylpropyl)amino]methyl]-3-pyridinemethanol dihydrochloride A solution of 263 mg of (R)-α-[[(1-methyl-2,2-dimethylpropyl)amino]methyl]tetrazolo[1,5-a]pyridine-6-methanol (Isomer A, Example 16), 0.08 ml of concentrated HCl and 455 mg of SnCl$_2$•2H$_2$O in 20 ml of methanol was heated at reflux for 16 hours. The reaction mixture was concentrated to dryness and partitioned between 2.5 N NaOH solution and an 80:20 methylene chloride:methanol mixture. The aqueous phase was repeatedly extracted and the combined organic layers back washed with saturated sodium chloride solution and dried with anhydrous magnesium sulfate. The solution was concentrated and the residue purified by preparative Tlc on silica gel (90:10:1 methylene chloride:methanol:NH4OH) to give 91 mg of product which was converted to its hydrochloride salt with ethanolic HCl (120 mg).

Likewise, a solution of 243 mg of Isomer B (Example 16), 0.08 ml of concentrated HCl and 420 mg of SnCl$_2$•2H$_2$O in 20 ml of methanol was heated at reflux for 16 hours. The solution was concentrated, partitioned between 2.5 N NaOH solution and 80:20 methylene chloride:methanol and then purified by preparative Tlc on silica gel to give 176 mg of product. Treatment with ethanolic HCl afforded the hydrochloride salt.

EXAMPLE 16

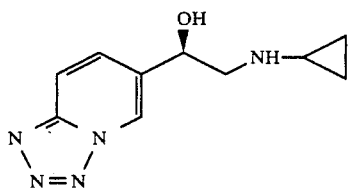

(R)-α[[(Cyclopropyl)amino]methyl]tetrazolo[1,5-a]pyridine-6-methanol

A solution of 375 mg (2.31 mmol) of (R)-2-(tetrazolo[1,5-a]pyrid-6-yl)oxirane and 652 mg (11.4 mmol) of cyclopropyl amine in 0.9 ml of absolute ethanol in a sealed reaction tube was heated at 100° C. for 3 hours. The reaction mixture was concentrated to dryness to yield 452 mg of crude product. Chromatography on silica gel (90:10:1 methylene chloride:methanol:conc. ammonium hydroxide) afforded 356 mg of product, m.p. 137°-39°.

EXAMPLE 17

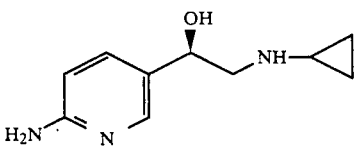

(R)-6-Amino-α-[[(cyclopropyl)amino]methyl]-3-pyridine methanol dihydrochloride To a solution of (R)-α-[[(cyclopropyl)amino]methyl-tetrazolo[1,5-a]pyridine-6-methanol (336 mg, 1.53 mmol) in 32 ml of methanol, 0.13 ml of 12 N HCl and 695 mg (3.08 mmol) of $SnCl_2\cdot 2H_2O$ were added. The mixture was heated at reflux for 24 hours and then treated with 5 ml of 2.5 N NaOH solution and 50 ml of an 80:20 methylene chloride:methanol mixture. The layers were separated and the aqueous phase repeatedly extracted with 80:20 methylene chloride:methanol. The combined organic layers were dried over anhydrous magnesium sulfate and concentrated to dryness, 376 mg. Purification by preparative Tlc on silica gel (90:10:1 methylene chloride:methanol:conc. ammonium hydroxide) gave 146 mg of pure product. This material was dissolved in ethanol and treated with an ethanolic HCl solution. Treatment of this solution with ether afforded the hydrochloride salt, 155 mg; $[\alpha]^{25}D = -38.5$ (MeOH). Analysis Calcd. for $C_{10}H_{15}N_3O\cdot 2HCl$:

C, 45.12; H, 6.44; N, 15.79; Cl, 26.64. Found: C, 45.34; H, 6.48; N, 15.83; Cl, 26.77.

EXAMPLE 18

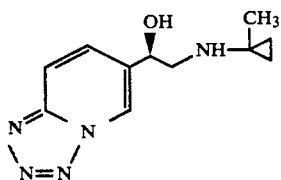

(R)-α-[[(1-Methylcyclopropyl)amino]methyl]tetrazolo[1,5-a] pyridine-6-methanol

A solution of 375 mg (2.31 mmol) of (R)-2-(tetrazolo[1,5-a]pyrid 6-yl)oxirane and 950 mg of (1-methylcyclopropyl)amine in 1 ml of absolute ethanol was heated at 70° C. for 4 hours in a sealed reaction tube. The reaction mixture was concentrated under reduced pressure and the residue chromatographed on silica gel plates (95:5:1 methylene chloride: methanol:conc. ammonium hydroxide) to give 338 mg of product, m.p. 72°–73° C.

EXAMPLE 19

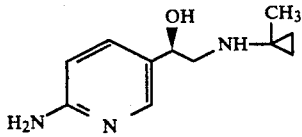

(R)-6-Amino-α-[[(1-methylcyclopropyl)amino]methyl]-3-pyridinemethanol dihydrochloride To a solution of 319 mg (1.37 mmol) of (R)-α-[[(1-methylcyclopropyl)amino]methyl]tetrazolo [1,5-a]pyridine-6-methanol in 25 ml of methanol, 0.12 ml of 12 N HCl and 622 mg (2.75 mmol) of $SnCl_2\cdot 2H_2O$ were added. This mixture was heated at reflux for 8 hours and then concentrated to dryness. The residue was partitioned between 80:20 methylene chloride:methanol and 5 ml of 2.5 N NaOH solution. The layers were separated and the aqueous layer repeatedly extracted with 80:20 methylene chloride:methanol. The combined extracts were dried with anhydrous magnesium sulfate and concentrated under reduced pressure, wt. 355 mg. Purification was accomplished by preparative Tlc on silica gel (90:10:1 methylene chloride:methanol:conc. ammonium hydroxide) to give 116 mg of product which was converted into its hydrochloride salt in ethanolic HCl. The salt was precipitated with ether, 105 mg; $[\alpha]^{25}D = -28.5$ (MeOH, c=1.5); Analysis: Calcd. for $C_{11}H_{17}N_3O\cdot 2HCl$:

C, 47.71; H, 6.78; N, 14.99. Found: C, 47.37; H, 6.93; N, 14.87.

EXAMPLE 20

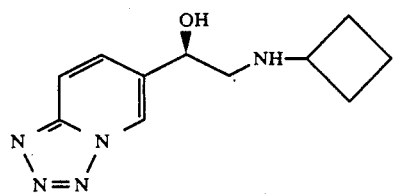

(R)-α-[[(Cyclobutyl)amino]methyl]tetrazolo[1,5-a]pyridine-6-methanol

A solution of 0.75 g (4.62 mmol) of (R)-2-(tetrazolo[1,5-a]pyrid 6-yl)oxirane and 1.838 ml (22.8 mmol) of cyclobutyl amine in 1.8 ml of absolute ethanol was heated at 100° C. in a sealed reaction tube for 2 hours. The reaction mixture was concentrated to dryness under reduced pressure, wt. 0.997 g. Tlc, mass spectrum and 1H NMR spectra are consistent with good purity and chemical structure.

EXAMPLE 21

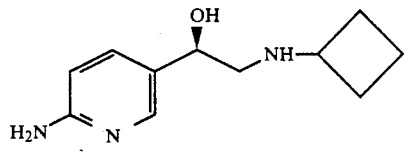

(R)-6-Amino-α-[[(cyclobutyl)amino]methyl]-3-pyridinemethanol dihydrochloride

A solution of 0.997 g of crude (R)-α-[[(cyclobutyl)amino]methyl]tetrazolo[1,5-a]pyridine- 6-methanol and 1.918 g of $SnCl_2\cdot 2H_2O$ in 89 ml of methanol was heated at reflux for 30 hours with stirring and under an inert atmosphere. The reaction mixture was concentrated to dryness and then partitioned between methylene chloride and 10% NaOH solution. The layers were separated and the aqueous phase repeatedly extracted with methylene chloride. The combined organic layers were dried with anhydrous magnesium sulfate and then concentrated to dryness, wt. 919 mg. The product was purified by preparative Tlc on silica gel (77:20:3 ethyl acetate:methanol: triethylamine) to give 529 mg of product. Treatment of this material with an ethanolic HCl solution followed by dilution with ether afforded the hydrochloride salt, 555 mg; $[\alpha]^{25}D = -33.8$ (MeOH); Analysis: Calcd. for $C_{11}H_{17}N_3O\cdot 2HCl$:

C, 47.15: H, 6.83; N, 15.00; Cl, 25.31. Found: C, 47.31, H, 7.16; N, 14 79; Cl, 25.05.

EXAMPLE 22

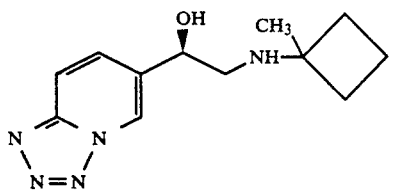

(R)-α-[[(1-Methylcyclobutyl)amino]methyl]tetrazolo[1,5-a] pyridine-6-methanol

A solution of 375 mg (2.31 mmol) of (R)-2-(tetrazolo [1,5-a]pyrid-6-yl)oxirane and 972 mg (11.42 mmol) of (1-methylcyclobutyl)amine [*J. Am. Chem. Soc.*, 83, 2723 (1961)] in 0.9 ml of absolute ethanol was heated at 70° C. for 3 hours with stirring under nitrogen. The reaction mixture was then concentrated to dryness (wt. 547 mg) and the residue purified by preparative Tlc on silica gel (95:5:1 methylene chloride:methanol:conc. ammonium hydroxide) to give 402 mg of product.

EXAMPLE 23

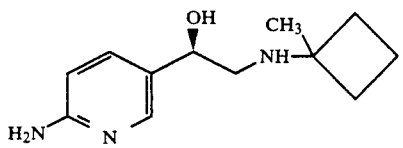

(R)-6-Amino-α-[[(1-methylcyclobutyl)amino]methyl]-3-pyridinemethanol dihydrochloride To a solution of 372 mg of (R)-α-[[(1-methylcyclobutyl)amino]methyl]tetrazolo[1,5-a]pyridine-6-methanol and 0.13 ml of 12 N HCl in 31 ml of methanol, 681 mg of SnCl$_2$•2H$_2$O was added and the resulting mixture heated at reflux for 16 hours. The reaction mixture was concentrated under reduced pressure and then partitioned between 80:20 methylene chloride:methanol and 2.5 N NaOH. The layers were separated and the aqueous layer further extracted with the same organic mixture. The combined extracts were dried with anhydrous magnesium sulfate and then concentrated. The residue (wt. 392 mg) was purified by preparative Tlc on silica gel (90:10:1 methylene chloride:methanol:-conc. ammonium hydroxide) to give 204 mg of product which was converted to its hydrochloride salt (ethanolic HCl/Ether), wt. 220 mg; $[\alpha]^{25}D = -28.4$ (MeOH, c=1.55); Analysis: Calcd. for C$_{12}$H$_{19}$N$_3$O•2HCl:

C, 48.99; H, 7.19; N, 14.34. Found: C, 49.29; H, 7.31; N, 13.98.

EXAMPLE 24

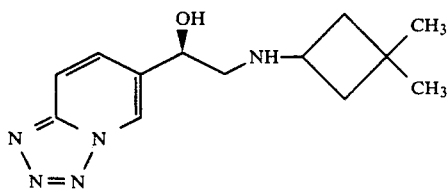

(R)-α-[[(3,3-Dimethylcyclobutyl)amino]methyl]tetrazolo [1,5-a]pyridine 6 methanol A solution of (R)-2-(tetrazolo[1,5-a]pyrid-6-yl)oxirane (375 mg, 2.31 mmol) and (3,3-dimethylcyclobutyl)amine (1.14 g, 11.5 mmol) in 0.8 ml of absolute ethanol was heated at 70° C. in a sealed reaction vessel for 3 hours. The reaction mixture was concentrated and the residue was purified by preparative Tlc on silica gel (90:10:1 methylene chloride:methanol:NH$_4$OH) to give 628 mg of product; Analysis: Calc'd. for C$_{13}$H$_{19}$N$_5$O:

C, 59.75; H, 7.33; N, 26.80. Found: C, 59.75; H, 7.04; N, 26.43.

EXAMPLE 25

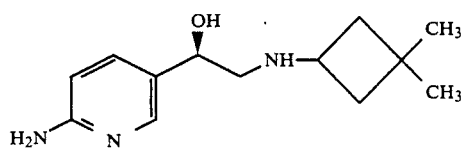

(R)-6-Amino-α-[[(3,3-dimethylcyclobutyl)amino]methyl]-3-pyridinemethanol

A solution of 403 mg (1.54 mmol) of (R)-A-[[(3,3-dimethylcyclobutyl)amino]methyl]tetrazolo [1,5-a]pyridine-6-methanol, 701 mg of SnCl$_2$•2H$_2$O and 0.13 ml of 12 N HCl in 32 ml of methanol was heated at reflux for 16 hours with stirring. At the end of this time period, the reaction mixture was concentrated to dryness under reduced pressure and the residue treated with 2.5 N NaOH and an 80:20 mixture of methylene chloride: methanol. The layers were separated and the aqueous layer further extracted with the same solvent system. The combined organic phases were dried with anhydrous magnesium sulfate and concentrated. The residue, 307 mg, was purified by preparative Tlc on silica gel (90:10:1 methylene chloride:methanol:NH$_4$OH) to give 214 mg of the free base. This material was dissolved in ethanol, treated with an ethanolic HCl solution and then precipitated as its hydrochloride salt from solution with ether, wt. 222 mg; $[\alpha]^{25}D = -28.9$ (MeOH, c=1.52).

EXAMPLE 26

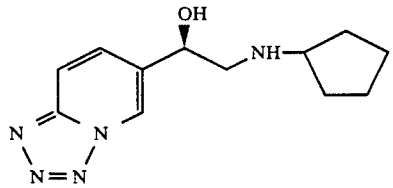

(R)-α-[[(Cyclopentyl)amino]methyl]tetrazolo[1,5-a]pyridine 6-methanol

A solution of 250 mg (1.54 mmol) of (R)-2-(tetrazolo[1,5-a]pyrid-6-yl)oxirane and 0.751 ml (7.61 mmol) of cyclopentyl amine in 0.6 ml of absolute ethanol was heated at 100° C. for 3 hours in a sealed reaction tube. The reaction mixture was concentrated to dryness and the residue (375 mg) purified by preparative Tlc on silica gel (90:10:2 ethyl acetate: methanol:triethylamine) to give 287 mg of pure product.

EXAMPLE 27

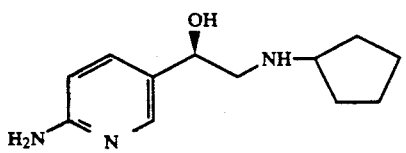

(R)-6-Amino-α-[[(cyclopentyl)amino]methyl]-3-pyridine methanol dihydrochoride

To a solution of 271 mg (1.16 mmol) of (R)-α-[[(cyclopentyl)amino]methyl]tetrazolo[1,5-a]pyridine-6-methanol in 24 ml of methanol, 521 mg (2.31 mmol) of $SnCl_2 \cdot 2H_2O$ was added and the resulting suspension heated at reflux for 20 hours. The reaction mixture was concentrated and the residue partitioned between 10% aqueous NaOH solution and methylene chloride. The layers were separated and the aqueous layer repeatedly extracted with methylene chloride. The combined organic extracts were washed with saturated NaCl solution and dried with anhydrous magnesium sulfate. Concentration and purification on silica gel (preparative Tlc) with 77:20:3 ethyl acetate:methanol: triethylamine as eluant afforded 157 mg of product. This free base was converted into its hydrochloride salt with ethanolic HCl solution and precipitated with ether to give 164 mg of the titled product: $[\alpha]^{25}D = -34.9$ (MeOH, c=1.86).

EXAMPLE 28

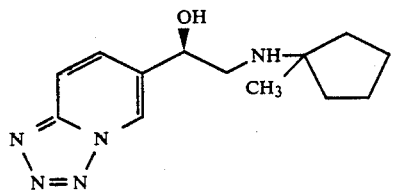

(R)-α-[[(1-Methylcyclopentyl)amino]methyl]tetrazolo[1,5-a]pyridine-6-methanol

A solution of (R)-2-(tetrazolo[1,5-a]pyrid-6-yl)oxirane (375 mg, 2.31 mmol) and (1-methylcyclopentyl)amine (229 mg, 2.31 mmol) in 10 ml of absolute ethanol was heated at reflux for 20 hours. The reaction mixture was concentrated to dryness and the residue (532 mg) purified by preparative Tlc on silica gel (90:10:1 methylene chloride:methanol: NH4OH) to afford 375 mg of product.

EXAMPLE 29

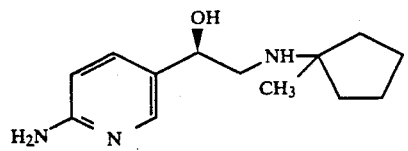

(R) 6-Amino-α-[[(1 methylcyclopentyl)amino]methyl]-3-pyridinemethanol dihydrochloride To a solution of 349 mg of (R)-α-[[(1-methyl cyclopentyl)amino]methyl]tetrazolo[1,5-a]pyridine-6-methanol and 0.11 ml of 12 N HCl in 28 ml of methanol, 609 mg of $SnCl_2 108 \cdot 2H_2O$ was added and the resulting mixture heated at reflux with stirring for 16 hours. The reaction mixture was concentrated to dryness and the residue partitioned between 25 ml of 80:20 methylene chloride:methanol and 5 ml of 2.5 N NaOH solution. The layers were vigorously stirred and then separated. The aqueous layer was repeatedly extracted with methylene chloride/methanol. The combined extracts were dried with anhydrous magnesium sulfate and concentrated to give 473 mg of crude product. Purification was affected on silica gel prep Tlc plates (80:20:1 methylene chloride: methanol:NH4OH) to give 153 mg of product. Treatment with ethanolic HCl solution followed by precipitation with ether afforded the hydrochloride salt, 140 mq. Analysis: Calc'd. for $C_{13}H_{21}N_3O \cdot 2HCl$:

C, 50.65; H, 7.52; N, 13.63. Found: C, 50.77; H, 7.63; N, 13.63.

EXAMPLE 30

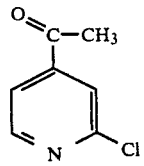

2-Chloro-4-acetylpyridine

To a solution of 20.4 g of 2-chloro -4-cyanopyridine in 290 ml of anhydrous ether at room temperature, 100 ml of 3.0 M methyl magnesium bromide in ether was slowly added under nitrogen. The mixture was stirred for 20 hours and then slowly poured onto cold aqueous hydrochloric acid. The layers were separated and the aqueous layer further extracted with ether. The combined organic layers were washed with saturated sodium chloride solution and then dried with anhydrous magnesium sulfate. The solution was concentrated and the residue chromatographed on silica gel (60:40 methylene chloride:hexane) to give 11.42 g of product.

EXAMPLE 31

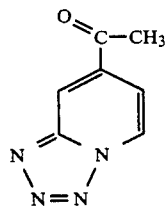

5-Acetyltetrazolo[1,5-a]pyridine

A solution of 11.42 g of 2-chloro-4-acetylpyridine, 9.51 g of sodium azide and 9.2 ml of 12 N HCl in 86 ml of a 1:1 ethanol:water mixture was heated at reflux for three hours. An additional 9.2 g of sodium azide was added and the reaction mixture heated at reflux overnight. An aqueous solution of sodium carbonate (3.92 g) was added and the mixture repeatedly extracted with methylene chloride. The combined extracts were washed with water and saturated sodium chloride solution and then dried with anhydrous magnesium sulfate. Concentration under reduced pressure afforded 10.2 g of product.

EXAMPLE 32

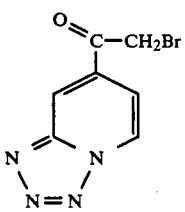

5-Bromoacetyltetrazolo[1,5-a]pyridine

To a cold solution of 10 g of 5-acetyltetrazolo [1,5-]pyridine in 120 ml of glacial acetic acid, 3.2 ml of bromine, 4.2 g of aluminum bromide and 2.0 ml of methanol were added and the reaction mixture stirred at room temperature for 3 hours. Dilution with 400 ml of water afforded a precipitate which was collected by filtration and washed with water. The solid was dissolved in methylene chloride and dried with anhydrous magnesium sulfate. Concentration gave 2.2 g of product.

EXAMPLE 33

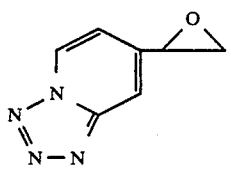

2-(tetrazolo[1,5-a]pyrid-5-yl)oxirane

To a cold ($-35°$ C.) solution of 10 g of 5-bromoacetyltetrazolo[1,5-a]pyridine in 40 ml of methanol, sodium borohydride (1.0 g) was added in portions. The reaction mixture was permitted to slowly come to room temperature. After 20 minutes the reaction mixture was concentrated and the residue dissolved in 50 ml of methylene chloride. The reaction mixture was cooled to $0°$ C. and 30 ml of a 10% NaOH solution was added with vigorous stirring. After 40 minutes the layers were separated and the aqueous layer further extracted with methylene chloride. The combined organic extracts were backwashed with saturated sodium chloride solution and dried with anhydrous magnesium sulfate. Concentration afforded 5.30 g of epoxide product.

EXAMPLE 34

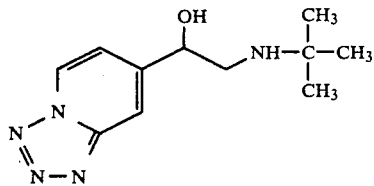

α[[(1,1-Dimethylethyl)amino]methyl]tetrazolo[1,5-a]pyridine-5-methanol

A solution of 1.2 g of 2-(tetrazolo[1,5-a]pyrid-5-yl)oxirane and 3.5 ml of tert. butylamine in 2.0 ml of absolute ethanol was heated at $60°$ C. for 3 hours. The mixture was then concentrated to afford a brown solid, 1.64 g. This material was purified by column chromatography on silica gel (95:5 methylene chloride:methanol then 95:5:1 methylene chloride: methanol:NH$_4$OH) to give 1.28 g of product.

EXAMPLE 35

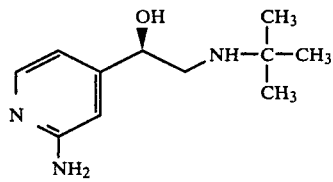

(R)-2-Amino-α-[[(1,1-dimethylethyl)amino]methyl]-4-pyridine methanol dihydrochloride A solution of 1.20 g of α-[[(1,1-dimethylethyl)amino]methyl]tetrazolo[1,5-a]pyridine-5-methanol and 2.5 g of SnCl$_2$•2H$_2$O in 50 ml of methanol was heated at reflux under nitrogen for 16.5 hours. The reaction mixture was concentrated to dryness and then partitioned between methylene chloride:methanol (80:20) and 2.5 N NaOH solution. The mixture was vigorously shaken and then the layers separated. The aqueous phase was repeatedly extracted with methylene chloride:methanol (80:20). The combined organic extracts were washed with saturated sodium chloride solution and then dried with anhydrous magnesium sulfate. Concentration gave 849 mg of crude product. Chromatography on silica gel (95:5:2 methylene chloride:methanol:NH$_4$OH) afforded 549 mg of pure racemic product. This material was converted into its hydrochloride salt by treatment with ethanolic HCl. The desired (R) isomer can be isolated by either fractional crystallization with an optically pure acid or by chromatographic separation on a chiral column.

EXAMPLE 36

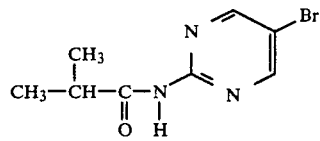

2-Isobutyramido-5-bromopyridine

A solution of 79 g of 2 amino-5-bromopyridine and 110 ml of isobutyric anhydride in 120 ml of methylene chloride was stirred at room temperature for 24 hours. To this mixture was added slowly 100 ml of 50% NaOH solution to hydrolyze excess anhydride. Water and additional methylene chloride were added and the layers separated. The aqueous layer was further extracted with methylene chloride and the combined organic extracts backwashed with water and dried with anhydrous magnesium sulfate. The solution was concentrated to afford 106.5 g of product.

EXAMPLE 37

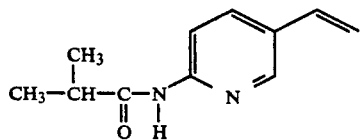

2-Isobutyramido-5-ethenylpyridine

A mixture of 9.72 g of 2 isobutyramido-5-bromopyridine, 0.49 g of tris-(0-tolyl)phosphine, 110 mg of palladium acetate, 10 ml of triethylamine and 30 ml of acetonitrile was heated at 80° C. in a glass lined vessel at 200 psi of ethylene for 18 hours. The reaction mixture was concentrated under reduced pressure and the residue chromatographed on el (0–25% ethyl acetate/methylene chloride) to give 6.67 g of pure product, m.p. 77°–8° C.; Analysis: Calc'd for $C_{11}H_{14}N_2O$:

C, 69.44; H, 7.42; N, 14.73. Found: C, 69.71; H, 7.32; N, 14.92.

EXAMPLE 38

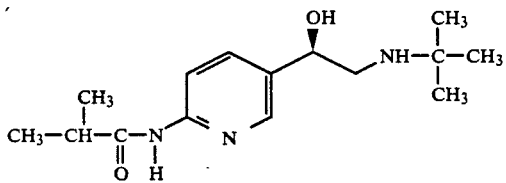

(R)-6-Isobutyramido-α-[(1,1-dimethylethyl)amino]methyl]-3-pyridinemethanol hydrochloride To a solution of 1.0 g of 2-Isobutyramido-5-ethenylpyridine in 8 ml of tetrahydrofuran, 4 ml of water and 0.94 g of N-bromosuccinimide were added and the reaction mixture stirred at room temperature for 3 hours. Tert.-butylamine (1 ml) was added to the reaction mixture which was then stirred for 20 hours at room temperature. The reaction mixture was then concentrated under reduced pressure and the residue partitioned between methylene chloride and water. The organic phase was concentrated and then purified by preparative Tlc on silica gel (10% ethyl acetate in methylene chloride) to give 0.26 g of epoxide. This material was dissolved in 4 ml of ethanol and treated with 1 ml of tert.-butylamine at 80° C. for 4.5 hours. The reaction mixture was concentrated and the residue purified by preparative Tlc on silica gel (25% acetone in ethyl acetate) to give two isomeric products: 132 mg of 2-isobutyramido-5-[1-[(1,1-dimethylethyl)amino]-2-hydroxy]ethylpyridine and 80 mg of 6-isobutyramido-α-[[(1,1-dimethylethyl)amino]methyl]-3-pyridine methanol. The titled product (39 mg) was dissolved in absolute ethanol and treated with 2.0 M ethanolic HCl to afford upon concentration 47 mg of the hydrochloride salt. The desired R-isomer can be isolated by either fractional crystallization with an optically pure acid or by chromatographic separation on a chiral column.

EXAMPLE 39

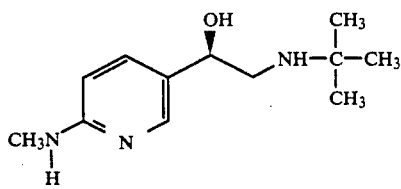

(R)-6-Methylamino-α-[[(1,1-dimethylethyl)amino]methyl]-3-pyridinemethanol hydrochloride A solution of 1.87 g of 5-ethenyl-2-(isobutyramido)-pyridine in 20 ml of dry dimethylformamide (DMF) was treated with 0.51 g of 50% sodium hydride in mineral oil under an inert dry atmosphere. The reaction mixture was stirred for 45 minutes at room temperature and then treated with 1.25 ml of methyl iodide. The mixture was stirred for 15 hours and then concentrated under reduced pressure. The residue was dissolved in methylene chloride and passed through a silica gel plug (25 g) and eluted with 25% ethyl acetate/methylene chloride. The filtrate was concentrated and the residue chromatographed on a silica gel column (0–25% ethyl acetate in methylene chloride) to give 1.75 g of the methylated material. This material was dissolved in 14 ml of tetrahydrofuran and treated with 1.52 g of N-bromosuccinimide and 7 ml of water. The reaction mixture was stirred at room temperature overnight and then partially concentrated. The aqueous residue was repeatedly extracted with methylene chloride. The organic layers were concentrated and the residue (4 g) chromatographed on silica gel (0–50% ethyl acetate in methylene chloride) to give 1.19 g of bromohydrin. This bromohydrin was dissolved in 6 ml of ethanol and treated with 1.0 ml of tert-butylamine. The reaction mixture was stirred at room temperature overnight and then concentrated under reduced pressure. The residue was chromatographed on silica gel (ethyl acetate then 25:75:2 methanol:methylene chloride:concentrated ammonia) to give 0.78 g of crude product. This material was further purified by preparative Tlc on silica gel (20% methanol in methylene chloride) to give 0.52 g of pure product. This material (0.44 g) was deblocked by treatment with 0.53 g of KOH in 5 ml of ethanol for 15 hours at 70° C. The reaction mixture was concentrated and the residue purified (2×) by preparative Tlc on silica gel (90:10:1 methylene chloride:methanol:concentrated aqueous ammonia) to give 162 mg of 6-methylamino-α-[[(1,1-dimethylethyl)amino]methyl]-3-pyridinemethanol. This material was dissolved in ethanol and treated with excess ethanolic HCl to afford 165 mg of the hydrochloride salt, m. p. 200° C. (dec). The desired R-isomer can be isolated by either fractional crystallization with an optically pure acid or by chromatographic separation on an optically active column.

EXAMPLE 40

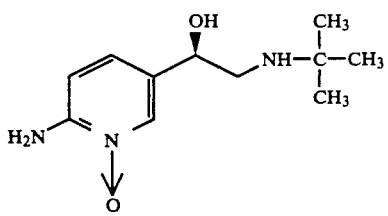

(R)-6-Amino-α-[[(1,1-dimethylethyl)amino]methyl]-3-pyridinemethanol-1-oxide

A solution of 1.76 g of free base (R)-6- amino-A -[[(1,1-dimethylethyl)amino]methyl]-3-pyridinemethanol (Example 3) and 10 ml of acetic anhydride in 20 ml of pyridine was stirred under nitrogen at room temperature for 14 hours. The reaction mixture was then concentrated under reduced pressure and the residue chromatographed on silica gel (1:1 ethyl acetate:methylene chloride then 5% methanol/ethyl acetate) to give 1.85 g of triacetate.

A solution of 1.53 g of this triacetate and 0.95 g of m-chloroperbenzoic acid in 15 ml of methylene chloride was stirred at room temperature for two hours. The reaction mixture was then chromatographed directly on silica gel (0–25% methanol/ethyl acetate) to afford 1.34 g of N-oxide.

The N oxide (1.55 g, multiple experiments) in 10 ml of methanol was treated with 0.62 ml of a methanolic KOH solution (397 mg KOH in 10 ml methanol) at room temperature for 3 hours. The reaction mixture was partially concentrated under reduced pressure and then chromatographed on silica gel (35% methanol/ethyl acetate) to give 1.18 g of monoacetate. This material (217 mg) was retreated with 2.3 ml of the methanolic KOH solution for 15 minutes at which point Tlc confirmed the disappearance of monoacetate. The reaction mixture was partially concentrated and then purified by preparative Tlc on silica gel (80:20:2 methylene chloride:methanol:NH4OH) to give 156 mg of final product.

EXAMPLE 41

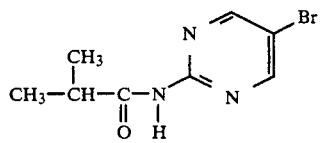

5-Bromo-2-(isobutyramido)pyrimidine

A suspension of 20 g of 2-amino-5-bromopyrimidine [*Chem. Abstr.*, 54, 11037 (1960)] and 14.78 g of 4-dimethylaminopyridine in 200 ml of pyridine was treated with 80 ml of isobutyric anhydride. The reaction mixture was then heated at 100° C. for 23 hours. The mixture was cooled and then diluted with 1500 ml of water. The mixture was thoroughly mixed for 30 minutes and then extracted with ether (3×300 ml). The ether extracts were washed with saturated sodium chloride solution (3×300 ml) and then dried over anhydrous magnesium sulfate. Concentration of the organic solution afforded 22.39 g of crude product which upon recrystallization from benzene (50 ml) afforded 14.5 g of pure product, mp 145°–148° C.

EXAMPLE 42

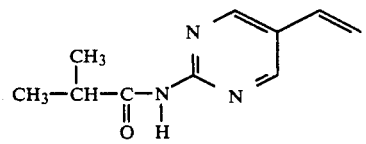

5-Ethenyl-2-(isobutyramido)pyrimidine

A glass-lined pressure vessel was charged with 4.85 g of 5-bromo-2-(isobutyramido)pyrimidine, 5.0 ml of triethylamine, 15 ml of acetonitrile, 245 mg of tris(O-tolyl)phosphine, and 55 mg of palladium acetate. The vessel was placed under an ethylene atmosphere at 200 psi and heated at 80° C. for 18 hours in a rocking autoclave. The vessel was cooled and then vented. The residue was treated with 50 ml of ether and the resulting mixture filtered. The solid was further washed with ether (2×25 ml). The organic filtrate was concentrated and then chromatographed on silica gel. Elution with methylene chloride:methanol (95:5) afforded 2.99 g of product, mp 110°–112° C.

EXAMPLE 43

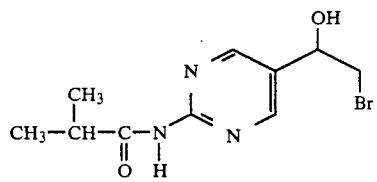

2-Isobutyramido-5-(1-hydroxyl-2-bromethyl)pyrimidine

To a solution of 764 mg of 5-ethenyl-2-(isobutyramido)pyrimidine in a mixture of 3 ml of water and 7 ml of tetrahydrofuran, 710 mg of N bromosuccinimide was added. The reaction mixture was stirred at room temperature for 18 hours and then partially concentrated under reduced pressure. To the aqueous residue 25 ml of methylene chloride was added and the layers separated. The aqueous layer was further extracted with methylene chloride (20 ml). The combined organic extracts were washed with 20 ml of water and then dried over anhydrous magnesium sulfate. Concentration afforded 977 mg of a glassy product. This material was chromatographed on silica gel (95:5 methylene chloride:methanol) to give 491 mg of pure bromohydrin.

EXAMPLE 44

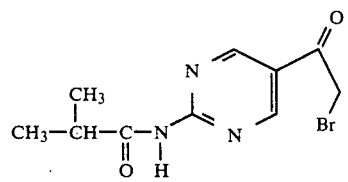

2-Isobutyramido-5-bromoacetyl)pyrimidine

To a solution of 2.29 g of 2-isobutyramido-5-(1-hydroxyl-2-bromoethyl)pyrimidine in 35 ml of methylene chloride and 20 ml of hexanes, 7.5 g of Manganese(IV) oxide (MnO$_2$) was added. The resulting mixture was stirred overnight at room temperature. The reaction mixture was diluted with 125 ml of chloroform and then filtered. The filtrate was concentrated to give 1.79 g of an oil which was chromatographed on silica gel (methylene chloride/ ether 90/10) to give 1.03 g of crystalline product, mp. 161°-163° C.

EXAMPLE 45

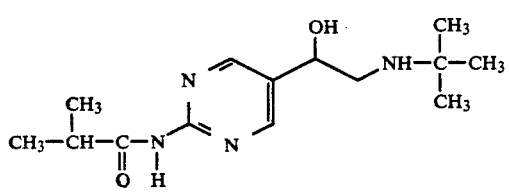

2-Isobutyramido-α-{[(1,1-dimethylethyl)amino]methyl}-5-pyrimidinemethanol

To a solution of 1.146 g of tert. -butylamine in 200 ml of dry acetonitrile, 2.05 g of solid 2-isobutyramido-5-(bromoacetyl)pyrimidine was added. The reaction mixture was stirred for 30 minutes and then gaseous hydrochloric acid was bubbled into the reaction mixture. The reaction mixture was then diluted with 300 ml of ether and the resulting precipitate collected by filtration. The precipitate was dissolved in 43 ml of anhydrous methanol and the resulting solution cooled to 5° C. Sodium borohydride (1.46 g) was slowly added (vigorous reaction) to this solution and the resulting mixture stirred for 1 hour in the cold. Acetic acid (5 ml) was added and then the pH of the reaction mixture was adjusted with concentrated aqueous ammonia to approximately pH 6. This solution was extracted with methylene chloride (3×50 ml). The combined extracts were washed with saturated sodium chloride solution and dried with anhydrous magnesium sulfate. The extracts were concentrated and the residue chromatographed on silica gel (90/10/1 methylene chloride/methanol/ ammonia) to afford 980 mg of product.

EXAMPLE 46

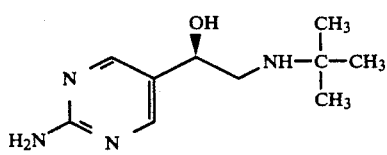

(R)-2-Amino-α-{[(1,1-dimethylethyl)amino]methyl}-5-pyrimidinemethanol Hydrochloride To a solution of 980 mg of 4-isobutyr-amido-α-{[(1,1-dimethylethyl)amino]methyl}-3-pyrimidinemethanol in 30 ml of ethanol, 1.51 g of potassium hydroxide in 4.5 ml of methanol was added. The resulting mixture was heated at 70° C. for 1.5 hours at which point the reaction mixture was concentrated under reduced pressure. The residue was dissolved in 10 ml of water and repeatedly extracted with a methylene chloride/methanol mixture (80/20). The combined organic layers were back-washed with saturated sodium chloride solution and concentrated to give 230 mg of product. This material was chromatographed on silica gel (methylene chloride/methanol/ammonia 90/10/1) to afford 208 mg of crystalline product. This material was dissolved in 2 ml of ethanol and was treated with 1 ml of a saturated ethanolic hydrochloric acid solution. To this solution 5 ml of ether was added and the resulting precipitate collected and dried to give 198 mg of the hydrochloride salt. The desired R-isomer can be isolated by either fractional crystallization with an optically pure acid or by chromatographic separation on a chiral column.

EXAMPLE 47

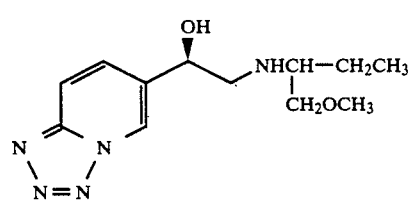

(R)-α-[[(2-(1-Methoxy)butyl)amino]methyl]tetrazolo[1,5-a]pyridine-6-methanol

A solution of 375 mg (2.31 mmol) of (R)-2-(tetrazolo[1,5-a]pyrid-6-yl)oxirane and 238 mg (2.31 mmol) of 2-amino 1-methoxybutane in 10 ml of absolute ehtanol was heated at reflux for 6 hours. The reaction mixture was concentrated under reduced pressure. The residue (wt. 589 mg) was purified by preparative Tlc on silica gel (95/5/10 methylene chloride/methanol/NH$_4$OH) to give 424 mg of a mixture of diastereomers. Analysis: Calc'd for C$_{12}$H$_{19}$N$_5$O$_2$:

C, 54.32; H, 7.22; N, 26.40. Found: C, 54.15; H, 7.19; N, 26.23.

EXAMPLE 48

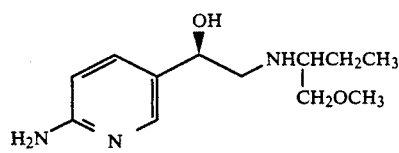

(R)-6-Amino-α-[[(2-(1-methoxy)butyl)amino]methyl]-3-pyridinemethanol dihydrochloride To a solution of 224 mg of (R)-α-[[(2-(1-methoxy)butyl)amino]methyl]tetrazolo[1,5-a]pyridine6-methanol in 17 ml of methanol, 0.07 ml of concentrated HCl and 389 mg (1.72 mmol) of SnCl$_2$•2H$_2$O were added and the mixture heated at reflux for 16 hours. The reaction mixture was concentrated to dryness and the residue dissolved in 80:20 methylene chloride:methanol. This solution was washed 5 times with 2.5 N NaOH solution and then dried with anhydrous magnesium sulfate. The solution was concentrated and the crude product purified by preparative Tlc on silica gel (90:10:1 methylene chloride:methanol:NH$_4$OH, eluted 3 times to afford 142 mg of a mixture of diastereomers. The product was dissolved in ethanol and treated with excess ethanolic HCl to give the hydrochloride salt upon dilution with ether, 120 mg, [α]$^{25}$D=39.3; Calc'd. for C$_{12}$H$_{21}$N$_3$O$_2$•2HCl:

C, 46.16; H, 7.42; N, 13.46; Cl, 22.7 Found: C, 45.89; H, 7.51; N, 13.65; Cl, 22.91.

What is claimed is:

1. A compound having the formula:

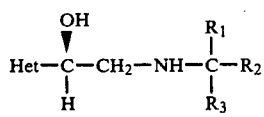

wherein $R_1$, $R_2$ and $R_3$ are independently selected from hydrogen, loweralky, loweralkenyl or loweralkynyl any of which may be optionally substituted with hydroxy or loweralkoxy, or $R_1$ and $R_2$ may be joined to form a cyclic ring of from 3 to 6 members in which the ring may further be substituted by lower alkyl;

Het is

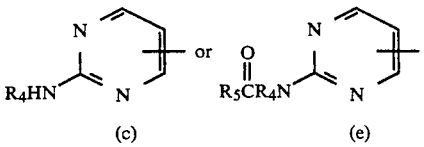

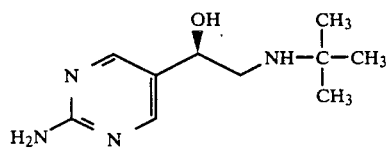

wherein $R_4$ and $R_5$ are independently hydrogen, loweralkyl, phenyl, substituted phenyl, phenylloweralkyl or substituted phenyl loweralkyl wherein the substituent is loweralkyl, loweralkoxy or halo, or the pharmaceutically acceptable acid addition salts thereof.

2. A compound of the formula:

3. A method for the promotion of growth and increasing the feed efficiency of animals which comprises administering to such animals an effective amount of a compound of claim 1.

4. A composition useful for promoting the growth and increasing the feed efficiency of animals which comprises an inert carrier and an effective amount of a compound of claim 1.

* * * * *